United States Patent [19]

Wallingford

[11] Patent Number: 5,098,390
[45] Date of Patent: Mar. 24, 1992

[54] HAND SYRINGE WITH SAFETY STORAGE FOR USED NEEDLE

[75] Inventor: Lawrence E. Wallingford, Garland, Tex.

[73] Assignee: Retractable I, Inc., Garland, Tex.

[21] Appl. No.: 579,021

[22] Filed: Sep. 7, 1990

[51] Int. Cl.⁵ .................................................. A61M 5/32
[52] U.S. Cl. .................................... 604/195; 604/110; 604/243
[58] Field of Search .................. 604/110, 195-197, 604/218, 240, 243

[56] References Cited

U.S. PATENT DOCUMENTS

| | | | |
|---|---|---|---|
| 4,507,117 | 3/1985 | Vining et al. | 604/196 |
| 4,675,005 | 6/1987 | DeLuccia | 604/110 |
| 4,874,382 | 10/1989 | Lindenmann et al. | 604/195 |
| 4,919,652 | 4/1990 | Alter et al. | 604/110 |
| 4,921,486 | 5/1990 | DeChellis et al. | 604/110 |
| 4,931,040 | 6/1990 | Haber et al. | 604/110 |
| 4,957,490 | 9/1990 | Byrne et al. | 604/197 |
| 5,000,736 | 3/1991 | Kaufhold, Jr. et al. | 604/110 |
| 5,000,738 | 3/1991 | LaVallo et al. | 604/110 |
| 5,019,043 | 5/1991 | Segui et al. | 604/110 |

FOREIGN PATENT DOCUMENTS 0347742  12/1989  European Pat. Off. ............ 604/110

*Primary Examiner*—John D. Yasko
*Assistant Examiner*—Adam J. Cermak

[57] ABSTRACT

An improved hand syringe has been provided which allows a used needle to be retracted completely into the body of the syringe, and stored there such that the spent needle cannot be used again. This improvement thereby provides safety from accidental infection to persons required to use hand syringes as well as persons required to disposed of these syringes.

4 Claims, 1 Drawing Sheet

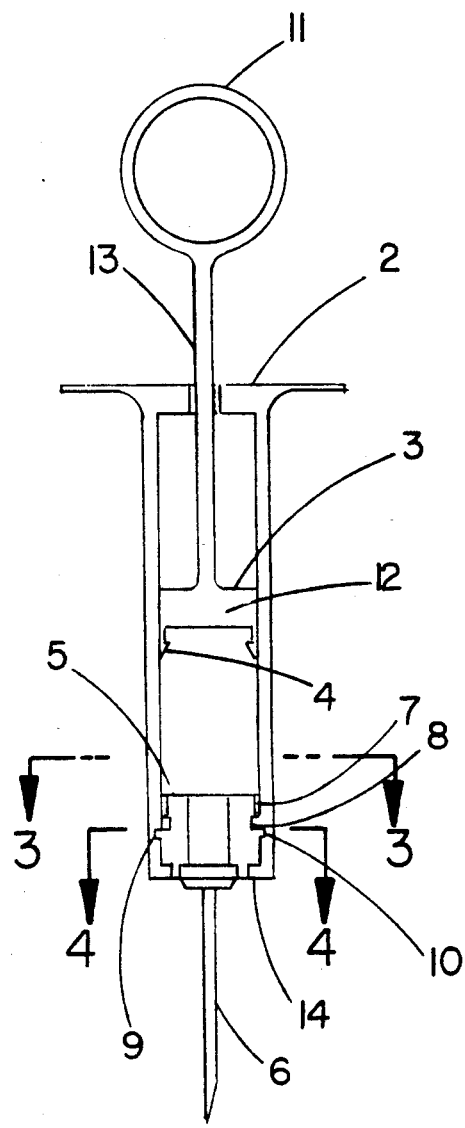
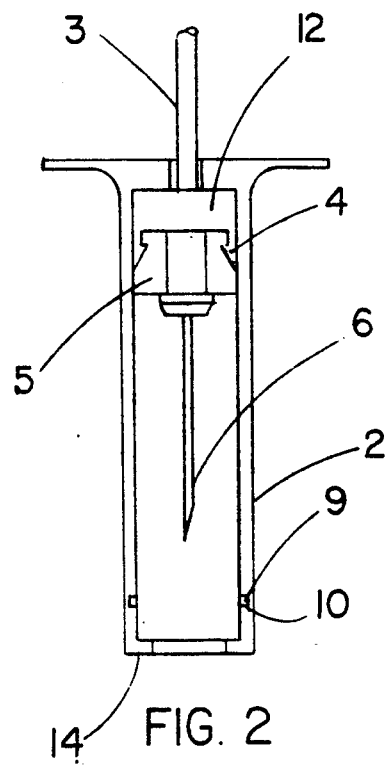
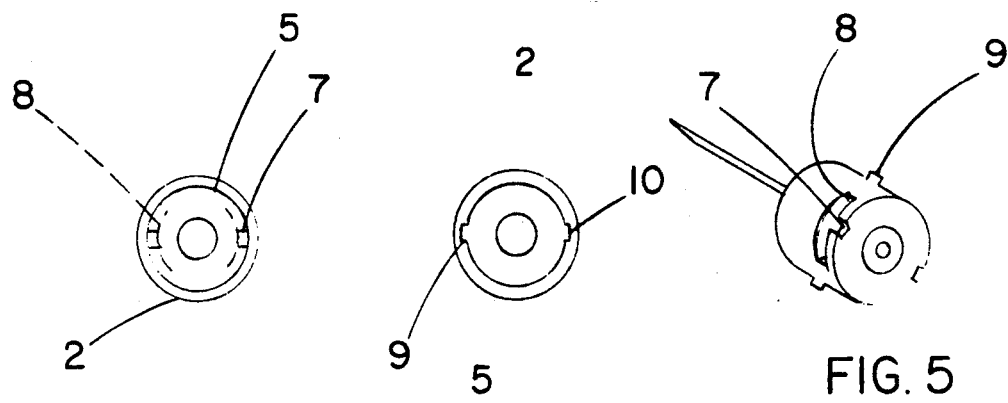
FIG. 1
FIG. 2
FIG. 3
FIG. 4
FIG. 5

HAND SYRINGE WITH SAFETY STORAGE FOR USED NEEDLE

SUMMARY

1. Prior Art

Prior art has taught means for enclosing a spent needle with a separate cover, breaking the used needle from the body of the syringe, spring actuation to push the needle back inside of the syringe body and several other approaches to eliminating secondary use of a hand syringe. Placing a cover over a used needle is not consistently done by the user, and breaking the needle is not a safe solution since users risks puncturing themselves while breaking the needle.

2. Objects of the Instant Invention

A primary object of the invention is to provide a convenient means to eliminate the secondary use of hand syringes thereby reducing the risk of transferring infection to otherwise healthy persons. A further object of the invention is to provide a convenient storage means for a used hand syringe needle that will prevent service personnel from accidentally becoming infected from a previously used hand syringe. A still further object of the invention is to to provide a syringe structure that is simple and will be economical to produce using present injection molding art.

BRIEF DESCRIPTION OF THE DRAWINGS

FIG. 1 is a section view illustrating the several components of the instant invention with the injection needle positioned for use.

FIG. 2 is a section view picturing the injection needle in a stored position.

FIG. 3 a section view taken along the line 3—3 in FIG. 1.

FIG. 4 is a section view taken along the line 4—4 in FIG. 1.

FIG. 5 is a pictorial view of the needle head

DETAILED DESCRIPTION OF THE INVENTION

Referring now to FIG. 1 in the drawings of reference the instant invention 1 is shown to comprise a body hollow cylindrical body 2, open on the distal end, that houses a sliding plunger 3, a needle head 5 seated contiguous to lip 14, that is secured within, and at the distal end of hollow cylindrical body 2 by tab 9 seated in recess 10 that is formed in the inside diameter of body 2.

Plunger 3 is made with a thumb eye 11 on one end, and external to the syringe body, connected to a piston 12 by means of shank 13. At least two locking tangs 4 extend downward from the bottom surface of piston 12.

The needle head 5 is formed with a standard syringe needle 6 of the appropriated size, at least two tang notches 7, and further, at least two circular slots 8 in the outside diameter of needle head 5.

The instant invention is used just as any other hand syringe. However, when the syrings needle 6 is stroked to completion, locking tangs 4 penetrate tang notches 7 allowing the lower face of piston 12 to come into intimate contact with the upper surface of needle head 5 at which time the plunger 3 is rotated several degrees in either clockwise or counter clockwise direction thereby causing the locking tangs 4 to be captured within slot 8. With the locking tangs 4 secured within slot 8 the plunger 3 is retracted causing the tabs 9 to tear away from the body of needle head 5 allowing needle head 5 to be retracted into the body 2 until the syringe needle 6 is encased by body 2, best seen in FIG. 2, and is now stored in a safe housing for disposal. The plunger shank 13 is now bent to one side of the body 2 thereby completely disabling the syringe for any further use.

FIG. 3 pictures a desired relationship of tang notch 7 with respect to the radial slots 8 in needle head 5.

FIG. 4 illustrates a suggested position of recess 10 with respect to tab 9.

FIG. 5 illustrates the relationship of tabs 9, tang notch 7, and radial slots 8 with respect to the needle head 5.

While the foregoing descriptions and drawings define the preferred embodiment of the instant invention, they do not preclude the many other means for accomplishing the same objectives that are within the scope and spirit of the instant invention.

What is claimed:

1. An improved method of storing and disposing of used syringe needles, after injection of a fluid into a diseased patient, thereby providing greater safety from accidental disease transmission to an individual responsible for making said injection, using a syringe comprising a hollow cylindrical body open on the distal end, a lip on said distal end, a needle head including a locking tab slot seated against said lip, a syringe needle secured to said needle head, and a sliding plunger including radial tabs that is moveable within said hollow cylindrical body, comprising the steps of:
   a. positioning said sliding plunger against the top surface of said needle head,
   b. insert said syringe needle into fluid container and sliding said plunger away from said needle head thereby filling said hollow cylindrical body with fluid,
   c. injecting said fluid into said patient by sliding said plunger toward the upper surface of the needle head,
   d. continue sliding said plunger until said radial locking tabs pass fully into said locking tab slot,
   e. rotate said sliding plunger thereby securing said locking tabs within the groove in the outside diameter of said needle head as said locking tab shoulder engages said groove,
   f. withdraw said sliding plunger causing radial tabs positioned upon the outside diameter of said needle head to be sheared,
   g. continue withdrawing said sliding plunger thereby retracting said needle head and said syringe needle until completely encased within said hollow cylindrical body,
   h. bending said shank of said sliding plunger thereby securing said needle head and said syringe needle in a safe position within said hollow cylindrical body.

2. In a syringe comprised of a hollow cylindrical body open on a distal end, whereas said distal end has a lip concentric with said hollow cylindrical body, said cylindrical body further has an opening in an upper end smaller than said opening at said distal end, said cylindrical body additionally provides an internal groove in proximity to said distal end, a sliding plunger within said cylindrical body, said plunger has an upward extending shank, said shank passes through said smaller opening in said upper end of said cylindrical body, said plunger has a piston on the distal end of said plunger, a needle head seated within said cylindrical body contiguous to said lip of said distal end of said cylindrical body, said needle head secured to a syringe needle, the improvement comprising;
  a. said plunger having a piston on its distal end with at least two locking tangs radially positioned on the outside diameter of said piston extending distally from the distal surface of said piston,
  b. said needle head having at least two locking tang notches radially positioned in alignment with said locking tangs of said piston, said locking tang notches having a width dimension to allow said locking tangs to pass therethrough, said locking tang notches intersecting, but not passing through a radial groove within the outside diameter of said needle head, said radial groove positioned in proximity of the upper surface of said needle head, said needle head further having a shearable radial shoulder positioned distally of said radial groove in said needle head, said shoulder being smaller in diameter than said groove in said cylindrical body, said needle head additionally secured to a syringe needle.

3. A plunger, as in claim 2, whereas said locking tangs have tapered shoulders.

4. A needle head as in claim 2, whereas said shearable shoulder is a series of intermittent tabs.

* * * * *